(12) United States Patent
Carr

(10) Patent No.: US 6,210,367 B1
(45) Date of Patent: Apr. 3, 2001

(54) INTRACORPOREAL MICROWAVE WARMING METHOD AND APPARATUS

(75) Inventor: Kenneth L. Carr, Harvard, MA (US)

(73) Assignee: Microwave Medical Systems, Inc., Acton, MA (US)

( * ) Notice: Subject to any disclaimer, the term of this patent is extended or adjusted under 35 U.S.C. 154(b) by 0 days.

(21) Appl. No.: 09/368,179

(22) Filed: Aug. 4, 1999

Related U.S. Application Data

(63) Continuation-in-part of application No. 08/977,747, filed on Nov. 25, 1997, now Pat. No. 6,146,359, which is a continuation-in-part of application No. 08/524,392, filed on Sep. 6, 1995, now Pat. No. 5,690,614.

(51) Int. Cl.$^7$ ..................................................... A61F 7/12
(52) U.S. Cl. ............................................................. 604/114
(58) Field of Search .................................. 604/114, 113, 604/500, 19, 28; 219/687, 688, 689

(56) References Cited

U.S. PATENT DOCUMENTS

| Re. 33,791 | 1/1992 | Carr ..................................... 374/122 |
| 4,346,716 | 8/1982 | Carr ..................................... 128/653 |
| 4,557,272 | 12/1985 | Carr ..................................... 128/736 |
| 4,583,556 | 4/1986 | Hines et al. .......................... 128/804 |
| 4,614,514 | 9/1986 | Carr et al. ........................... 604/113 |
| 5,073,167 | 12/1991 | Carr et al. ........................... 604/114 |
| 5,234,004 | 8/1993 | Hascoet et al. ...................... 607/116 |
| 5,364,336 | 11/1994 | Carr ......................................... 600/2 |
| 5,690,614 * | 11/1997 | Carr et al. ........................... 604/114 |
| 5,954,717 * | 9/1999 | Behl et al. ........................ 604/114 X |
| 6,087,636 * | 7/2000 | Farier, Jr. et al. ................ 604/114 X |

OTHER PUBLICATIONS

Larry M. Gentilello et al., "Continuous Arteriovenous Rewarming: Experimental Results and Thermodynamic Model Simulation of Treatment for Hypothermia", Copyright 1990 by the Williams & Wilkins Co., pp. 1436–1449.

\* cited by examiner

*Primary Examiner*—John D. Yasko
(74) *Attorney, Agent, or Firm*—Cesari and McKenna, LLP

(57) ABSTRACT

Intracorporeal warming apparatus includes a catheter for placement in a patient, the catheter having a distal end and a proximal end. An antenna lies adjacent to the distal end of the catheter and a cable having one end connected to the antenna extends from the proximal end of the catheter. A transmitter transmits a first signal of a first frequency capable of heating blood or tissue and a receiver receives a second signal of a second frequency which is indicative of thermal radiation, the receiver producing an output signal in response thereto. A diplexer connects the proximal end of the cable to the transmitter and receiver so as to couple the first signal from the transmitter only to the antenna and the second signal from the antenna only to the receiver so that the apparatus can simultaneously heat the blood or tissue and determine the actual temperature of that material. Preferably also, the catheter includes an expandable stand-off device adjacent to the antenna which can be expanded to properly position the catheter when in use. There is also provision for indicating the condition of the stand-off device, i.e., open or closed, before the apparatus is activated.

22 Claims, 2 Drawing Sheets

INTRACORPOREAL MICROWAVE WARMING METHOD AND APPARATUS

RELATED APPLICATION

This application is a continuation-in-part of Ser. No. 08/977,747, filed Nov. 25, 1997, now U.S. Pat. No. 6,146,359 which is a continuation-in-part of Ser. No. 08/524,392, filed Sep. 6, 1995, now U.S. Pat. No. 5,690,614.

BACKGROUND OF THE INVENTION

This invention relates to an intracorporeal microwave warming method and means. It relates more particularly to microwave apparatus including a catheter capable of being introduced into a patient's blood vessel or body cavity to provide uniform and controlled heating of fluid or tissue within the patient. The invention has particular application as an intravascular blood warmer for raising the body core temperature of a hypothermic trauma patient and so the invention will be described primarily in that context. It should be understood, however, that aspects of the invention have equal application in other contexts such as benign prostatic hyperplasia (BPH) ablation and myocardial ablation.

Hypothermia in trauma patients (i.e., body core temperature less than 35° C.), has been shown to be associated with high mortality. According to studies, trauma patients having a temperature less than 34° C. have a 60% mortality and those patients with a temperature less than 32° C. have a 100% mortality. The effects of hypothermia on trauma patients are numerous. For example, a decrease in core temperature results in decreased mental status, decrease heart rate and cardiac output and diminished renal blood flow. Hypothermia also results in prolonged clotting times and portal sequestration of platelets causing peripheral thrombocytopenia as well as decreased platelet function. The resultant coagulopathy may make futile all attempts at surgical control of traumatic bleeding.

There are currently several methods of rewarming a trauma patient in general use today. These include use of warm resuscitation fluids, airway rewarming, heating blankets, overhead radiant warmers, body cavity lavage, continuous arteriovenous rewarming (CAVR) and cardiopulmonary bypass. The most effective method of rewarming is currently cardiopulmonary bypass, but this technique is often unavailable and is technically difficult to perform. CAVR has been shown to be much more efficient than other standard rewarming techniques, but it requires cannulation of both the femoral artery and vein in order to connect the patient to a conventional external heat exchanger and it is somewhat work intensive. Furthermore, it results in loss of blood because a considerable amount of fluid is required in order to fill up or prime the various IV tubes connected to the warmer.

It would be desirable, therefore, to be able to provide a simple, efficient means of rewarming trauma patients, especially soldiers in combat who are significantly injured and therefore at risk for developing. Controlled intracorporeal heating for other reasons is also a desirable objective.

SUMMARY OF THE INVENTION

Accordingly, it is an object of the present invention to provide an improved technique for controlledly heating fluid or tissue in a patient.

Another object of the invention is to provide microwave warming apparatus for efficiently heating or rewarming fluid or tissue in a patient.

A further object of the invention is to provide such apparatus which provides uniform and controlled heating in a hypothermic trauma patient.

Another object is to provide such warming apparatus which requires only a single venous connection to a patient and which minimizes patient blood loss.

An additional object of the invention is to provide an improved intravascular microwave warming catheter which minimizes blockage of, and injury to, the blood vessel in which it is placed.

A further object of the invention is to provide intravascular microwave warmning apparatus which simultaneously monitors accurately the temperature of the blood during the warming process.

Another object of the invention is to provide microwave apparatus for controlledly ablating tissue within a patient.

Other objects will, in part, be obvious and will, in part, appear hereinafter.

The invention accordingly comprises the several steps and the relation of one or more of such steps with respect to each of the others, and the apparatus embodying the features of construction, combination of elements and arrangement of parts which are adapted to effect such steps, all is exemplified in the following detailed description, and the scope of the invention would be indicated in the claims.

Briefly, the intravascular blood warming technique specifically disclosed herein is intended to provide uniform and controlled heating in a hypothermic patient using microwave apparatus which safely and efficiently warms the patient's blood in order to raise the patient's body core temperature.

The warming apparatus comprises a relatively long, somewhat flexible intravascular catheter capable of being threaded through a conventional introducer to a major blood vessel such as the superior or inferior vena cava. At its distal end, the catheter incorporates an antenna and an expandable stand-off device which prevents the distal end of the catheter, and more particularly the antenna, from contacting the wall of the blood vessel and potentially overheating tissue at that wall. A single cable extending from the proximal end of the catheter is connected to an extracorporeal control and display unit which supplies power to and receives temperature-indicating signals from the catheter.

The control and display unit includes a microwave transmitter which produces a signal having a suitable heating frequency. That signal is applied by way of a diplexer to the cable leading to the antenna in the catheter. This causes the antenna to emit electromagnetic radiation capable of heating high dielectric/high loss organic material such as blood in the vicinity of the catheter.

Also, connected to the diplexer in the control and display unit is a microwave receiver preferably in the form of a radiometer. As is well known, radiometry is a technique for measuring electromagnetic radiation considered as thermal radiation. The single antenna in the catheter is able to detect the microwave radiation emitted by the material surrounding the catheter and that microwave signal is applied by way of the cable and diplexer to the receiver which produces an electrical signal indicative of the temperature of that material. That signal is applied by way of a processor to a display in the control and display unit which thereupon provides a visible indication o f that temperature. That temperature-indicating signal can also be used to enable the processor to control the transmitter so as to effect controlled heating of the material surrounding the catheter. As we shall see also, the control and display unit includes means for detecting whether the aforementioned stand-off device in the catheter is open or closed to ensure that the catheter is in the correct position in the blood vessel before the catheter's antenna is activated.

As will be described in more detail later, the diplexer in the control and display unit allows for the separation of the relatively low heating frequency of the transmitter from the much higher radiometer frequency. Resultantly, the apparatus can use a common antenna and cable connection to the control and display unit to both transmit (heat) and receive (measure temperature). Thus, the diplexer and associated radiometer eliminate the need for thermocouples or thermistors in the catheter thereby minimizing the cost of, and improving the performance and safety record of, the catheter. It should be emphasized in this connection that this cost and performance comparison is not being made between just a radiometer and a thermocouple, but rather with all of the ancillary parts such as wires, connectors and amplifiers that have to support the thermocouple. Elimination of all of these parts enhances the flexibility of the catheter and greatly improves the overall reliability and maintenance record of the apparatus.

Most importantly, since the present apparatus senses temperature using radiometry, the temperature sensed is the actual temperature of the blood surrounding the catheter rather than the catheter tip temperature as would be the case if the catheter incorporated a thermocouple or thermister for temperature detection and control.

Similar devices incorporating the invention can be used in other applications. In tissue ablation, for example, the configuration of the catheter depends upon the body cavity being accessed. Thus to treat BPH, a transurethral catheter or probe is used which may incorporate a conventional helical antenna and receive sufficient power to raise the patient's intraprostatic temperature sufficiently and for a sufficient time to selectively necrose the BPH. Such a catheter typically incorporates a cooling circuit adjacent the antenna to ensure that the patient's urethra is not heated above a safe temperature, and an expandable balloon to properly position the catheter; see U.S. Pat. No. 5,234,004, the contents of which is hereby incorporated herein by reference.

Transurethral microwave heating apparatus incorporating this invention would allow a common antenna in the catheter or probe to provide both heating and measurement of temperature, thereby eliminating the requirement of thermocouples and wires and allowing closer control over actual tissue temperature, as well as providing a positive indication of the condition of the catheter's expandable device. In this case, the expandable device, when open, would seat against the neck of the patient's bladder to properly locate to the catheter or probe.

When used for myocardial ablation, the present apparatus would include a catheter with an antenna and expandable stand-off device and be capable of being threaded into a patient's heart muscle in order to controlledly heat heart tissue in order to necrose said tissue. In this application, the expandable device is used to center the catheter.

Other applications for the invention may be envisioned.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF AN ILLUSTRATIVE EMBODIMENT

Figure 1:
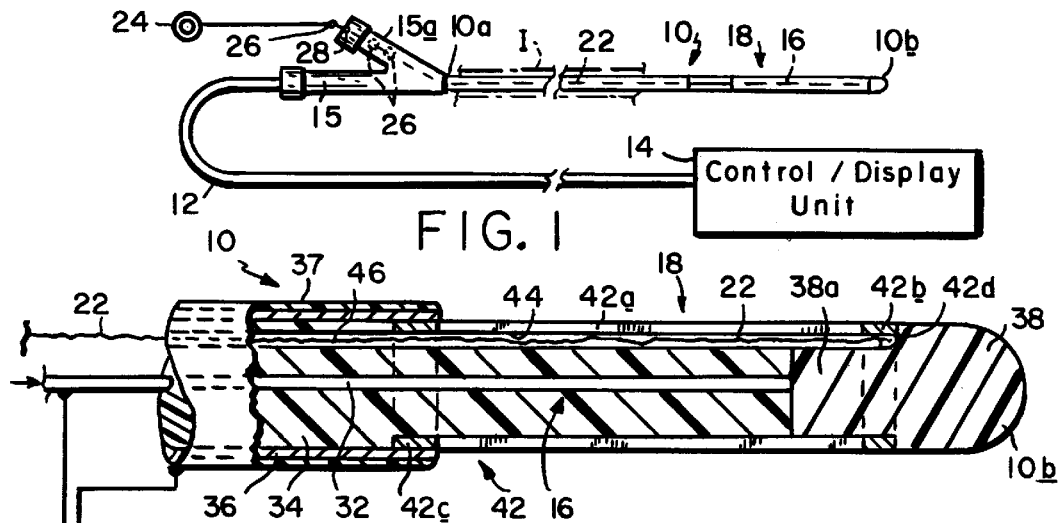
FIG. 1 is a diagrammatic view of intracorporeal microwave warming apparatus incorporating the invention.

Referring to FIG. 1 of the drawings, warming apparatus suitable for treating hypothermia comprises a relatively long catheter 10 connected by a single coaxial cable 12 to a control and display unit 14. Catheter 10, which may be designed a low-cost disposable device, has a proximal end 10a to which cable 12 is connected by way of a tubular fitting 15 and a distal end or tip 10b. Catheter 10 has a small diameter and is relatively flexible so that it can be threaded along a conventional introducer, e.g. 8.5 French, indicated in phantom at I in FIG. 1, allowing the distal end 10b of the catheter to be placed at a selected position in a patient's blood vessel V (FIG. 4), such as the superior or inferior vena cava. Typically, vessel V is accessed via a vein in the patient's neck.

Figure 3:
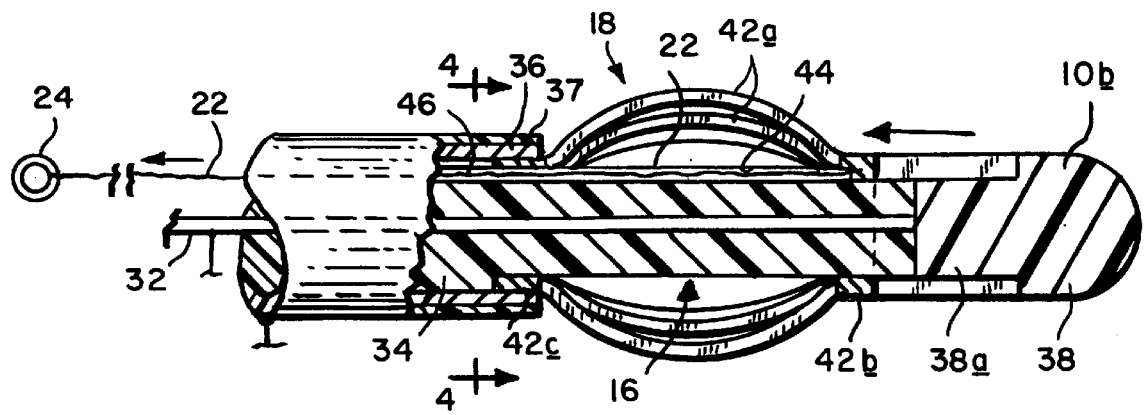
FIG. 3 is a similar view with the apparatus' stand-off device shown in its open or expanded position.
Figure 4:
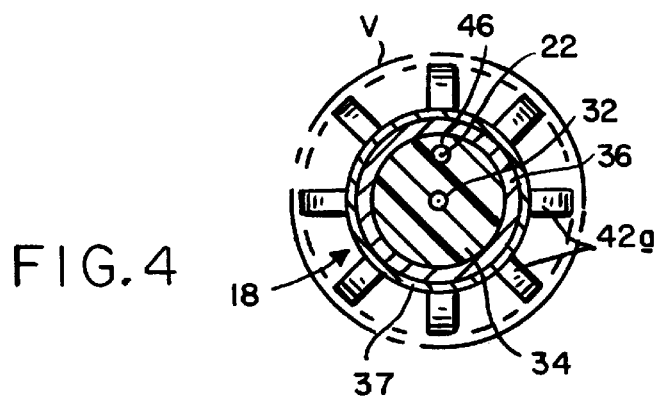
FIG. 4 is a sectional view taken along line 4—4 of FIG. 3.

When the catheter 10 is properly positioned as aforesaid, the control and display unit 14 supplies power to a microwave antenna 16 located adjacent to the distal end 10b of the catheter causing the antenna to emit electromagnetic radiation which warms the blood in the blood vessel surrounding the antenna. Preferably, catheter 10 also includes a stand-off device indicated at 18 adjacent to the antenna which can be moved from a closed position illustrated in FIGS. 1 and 2 and an open or expanded position shown in FIGS. 3 and 4. When the stand-off device 18 is closed, it is more or less cylindrical and has substantially the same cross-sectional size as the remainder of the catheter so that it does not interfere with the movement of the catheter along introducer 1 to and from the patient's blood vessel V. On the other hand, when the device 18 is moved to its open or expanded position upon placement of the catheter at the proper location in the patient's blood vessel V as shown in FIG. 4, the device 18 spaces the antenna 16 from the wall of that vessel thereby preventing excessive heating of, and damage to, the tissue comprising that wall.

In accordance with the invention, means are provided for moving the stand-off device 18 between its open and closed positions. In the catheter depicted in FIG. 1, the stand-off device 18 has an inherent bias or resilience which normally maintains that device in its closed position shown in FIG. 2. The device may be moved from that position to its open position shown in FIGS. 3 and 4 by means of a flexible cord 22 which extends from device 18 along the catheter and through a tubular branch 15a of fitting 15 to a ring 24. By pulling on the cord 22 using ring 24, the device 18 may be moved to its open position. The device can be maintained in that position by engaging one of a series of beads 26 on cord 22 in a notch 28 in the free end of the fitting branch 15a as shown in FIG. 1. When the tension on cord 22 is relieved, the stand-off device 18 will resume its normal cylindrical shape best seen in FIG. 2.

Figure 2:
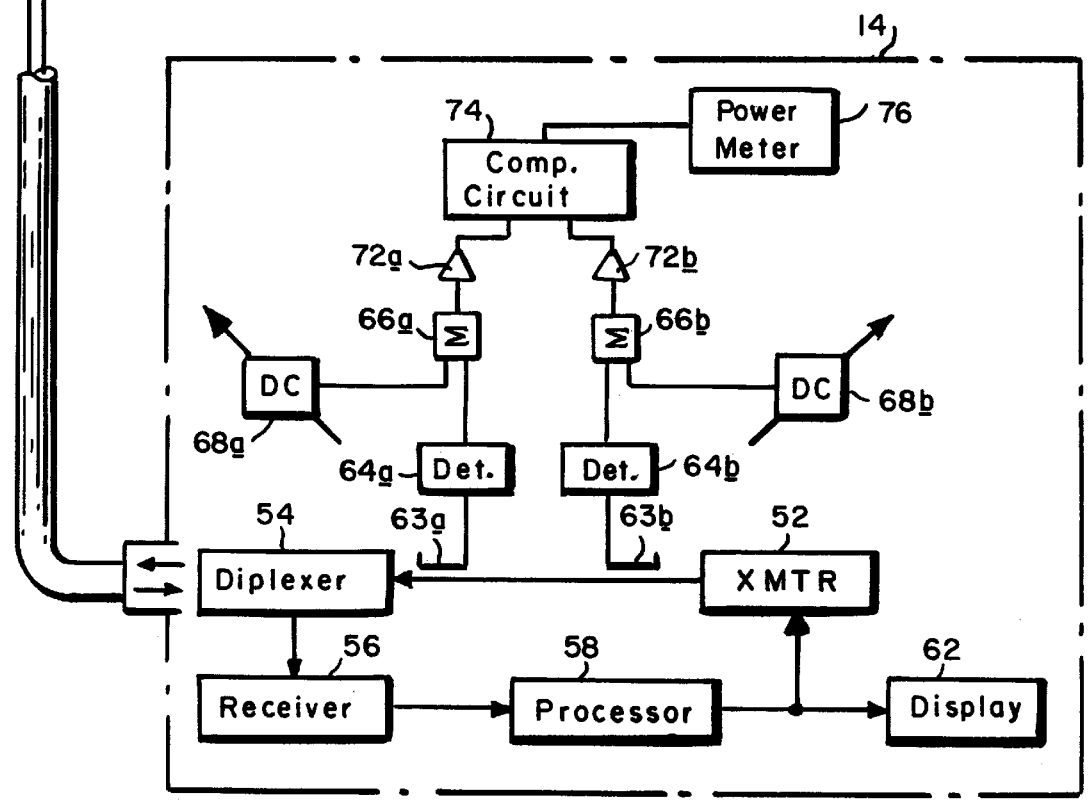
FIG. 2 is a fragmentary sectional view on a larger scale, with some parts shown diagrammatically, of the FIG. 1 apparatus showing the apparatus' stand-off device in its closed position.

As shown in FIG. 2, the catheter 10 comprises a central conductor 32 surrounded by a cylindrical body 34 of a suitable low loss dielectric material. Surrounding the dielectric body 34 is an outer conductor 36. At fitting 15, the proximal ends of conductors 32 and 36 are connected to the inner and outer conductors of coaxial cable 12. Preferably, a protective coating 37, e.g. of PTFE, covers outer conductor 36.

At a distal end segment of the catheter 10, the inner conductor 32 and dielectric body 34 extend beyond the outer conductor 36 to form the microwave antenna 16 which, in this case, is a monopole producing a relatively long radiation pattern. In some applications, a helical antenna may be used; see U.S. Pat. No. 4,583,556. Furthermore, the projecting segment of the body 34 has a reduced crossection to accommodate and provide clearance for the stand-off device 18. The distal end 10b of the catheter is actually formed by a rounded low loss dielectric button 38 having a cylindrical stem 38a which has the same diameter as the distal end of the dielectric body 34 so that the stem 38a can be butted and secured to the distal end of body 34 as shown in FIG. 2.

The stand-off device 18 comprises a cylindrical sleeve 42 of low dielectric/low loss material having an inside diameter which is slightly larger than the reduced diameter of body 34 and the button stem 38a. Sleeve 42 is slitted along its length to provide a circular array of flexible, resilient ribs 42a which extend between a distal annular sleeve end segment 42b encircling button stem 38a and a proximal annular sleeve end segment 42c encircling dielectric body 34 under the distal end of outer conductor 36. That is, the reduction in cross section of the dielectric body 34 extends under the distal end of outer conductor 36 to accommodate the sleeve segment 42c. End segment 42c is fixed by an adhesive or other means, while end segment 42b is slidable.

As best seen in FIG. 2, the dielectric body 34 and button stem 38a are grooved lengthwise at 44, that groove connecting with a longitudinal passage 46 in body 34 which extends to the fitting branch 15a to accommodate the cord 22. The distal end of cord 22 attached to a radially inner nub 42d on the slidable end segment 42b of sleeve 42, which nub slides along groove 44. Normally, sleeve 42 reposes in its closed position illustrated in FIG. 2, i.e., it has a cylindrical shape which falls within the envelope of the catheter 10. Therefore, the catheter is able to pass through introducer I (FIG. 1). However, when tension is applied to cord 22, the distal end segment 42b of the sleeve slides toward the proximal end segment 42c thereof causing the sleeve ribs 42a to flex and bow outward as shown in FIGS. 3 and 4, thereby greatly increasing the crossection of the stand-off device 18. In fact, the ribs 42a may be flexed to an extent that they contact the wall of the blood vessel V in which the catheter 10 is placed as shown in FIG. 4 so that the catheter antenna 16 is maintained in spaced relation to the vessel wall.

It is important to note that when the stand-off device 18 is in its open position shown in FIGS. 3 and 4, it does not appreciably obstruct blood flow through the patient's blood vessel V. Therefore, no hot spots are created in the blood adjacent antenna 16 as could occur if catheter 10 incorporated a conventional balloon-type stand-off device. In other words, blood is free to flow through and around the expanded ribs 42a so that there is no development of slow moving or stagnant "pools" of blood around the catheter that could be heated excessively by antenna 16.

When the tension on cord 22 is relieved, the resilient sleeve ribs 42a tend to resume their unflexed linear state so that the sleeve resumes it natural cylindrical shape thereby enabling the stand-off device 18 and catheter 10 as a whole to again pass through the introducer I (FIG. 1).

Still referring to the one disclosed in the above-identified patent applications, the contents of which are hereby incorporated by reference herein. More particularly, unit 14 comprises a microwave transmitter 52 which is preferably a solid state programmable transmitter which may operate at 915 MHz ($\lambda$T) and have a maximum power output of 0 to 120 watts. Such a transmitter is available from Microwave Medical Systems, Inc., Acton, Mass. (Part No. 190972). That transmitter provides, if desired, short-term operation with battery back up and automatic battery recharging when the unit is plugged into an operative AC outlet.

The output from the transmitter is coupled to coaxial cable 12 by way of a diplexer 54. That transmitted power causes antenna 16 to emit electromagnetic radiation. As the blood surrounding catheter 10 absorbs energy, its temperature is elevated.

The same antenna also detects the thermal radiation emitted by that fluid and applies a corresponding electrical signal via diplexer 54 to a microwave receiver 56, to wit: a radiometer, in control and display unit 14. A suitable radiometer is available from Microwave Medical Systems, Inc., Acton, Mass. (Part No. RAD-G1) It has a physical volume of only about 2 cubic inches and weighs only 3 ounces. It has a radiometer frequency of 3.7 to 4.2 GHz, with a center frequency of 4.0 GHz ($\lambda$R).

Due to the presence of the diplexer 54, the receiver 56 detects only that energy associated with the blood being heated. The temperature-indicating signal from receiver 56 may then be processed by a processor 58 in unit 14 to maintain the blood in vessel V at a selected temperature, e.g., normal body temperature, or to warm the blood according to a selected temperature vs time profile programmed into processor 58.

The processor 58 also controls a display 62 in unit 10 which can display in real time the patient's body core temperature and other useful information such as the selected temperature vs time profile, diagnostic data and the like.

Figure 5:
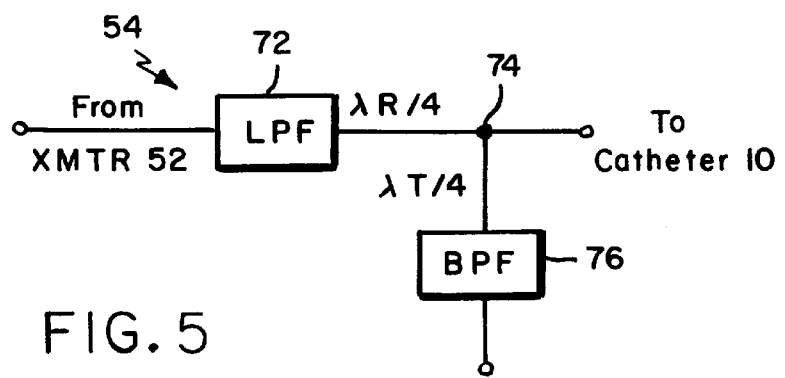
FIG. 5 is a diagrammatic view of the diplexer section of the FIG. 1 apparatus.

The diplexer 54, shown in detail in FIG. 5, separates the transmitter heating frequency $\lambda$T from the receiver center frequency $\lambda$R which allows the use of the common coaxial cable connection 12 to the common antenna 16. Basically, the diplexer has two arms each of which contains a microwave filter. More particularly, the diplexer includes a low pass filter 72 at the output port of transmitter 52 which passes only the transmitter signal $\lambda$T and a band pass filter 76 at the input port of the receiver 56 which passes the receiver signal $\lambda$R but blocks the out-of-band transmitter signal $\lambda$T. To further isolate the two signals, filter 72 is positioned a quarter wavelength (at $\lambda$R) from the junction 74 of the diplexer. This creates a low-loss, well-matched stub at that frequency. Likewise, the length of the connection of filter 76 to junction 74 is a quarter wavelength (at $\lambda$T) so that the arm acts as a short circuit. Resultantly, the transmitter signal is not coupled to the receiver arm of the diplexer (and vice versa), thereby minimizing transmission losses.

As mentioned above, after catheter 10 is positioned in the patient's blood vessel V, the stand-off device 18 is opened to space antenna 16 from the vessel wall to avoid tissue damage due to radiation from the antenna. It is quite important, then, for the physician to know the condition of the stand-off device 18, i.e., whether it is open or closed. Accordingly, the present apparatus includes novel means for indicating to the physician the condition of the device 18.

More particularly, as shown in FIG. 2, the microwave transmitter 52 incorporates two directional couplers 63a and 63b to sample both forward and reflected power. These sampled outputs are applied to two detectors 64a and 64b, respectively shown in FIG. 2 which provide video samples of the forward and reflected power. The detectors operate in their square-wave region which means that each detector output is proportional to the microwave power in watts. In the case of forward power, the detector 64a output is summed in a summing circuit 66a with the output from an adjustable DC offset source 68a, gained in an operational amplifier 72a and applied to a computational circuit 74 which is basically a one-quadrant divider with a fixed scale factor. For reflected power, the detector 64b output is summed at 66b with a DC offset voltage from adjustable source 68b, gained in an amplifier 72b and applied to circuit 74. The output of circuit 74 is given by $$V_0 = 2(P_{REFL}/P_{FWD})$$

where:

$V_0$ is the multiplier output in volts applied to the % reflected power meter, $P_{REFL}$ is the detected reflected power, and $P_{FWD}$ is the detected forward power.

The circuit 74 output, which is proportional to the power ratio, is applied to a power meter 76 which thereupon displays the % of forward power reflected, and is thus an indication of the reflection coefficient or load match to the transmitter 52. If desired, the function of circuit 72 could be incorporated into processor 58 and the meter 76 incorporated into display 62 to simplify the control and display unit 14.

The measurement of reflected power, i.e. the meter 76 reading, is used to determine the position of the stand-off device 18 (i.e., open or closed). More particularly, the antenna 16 will be well matched when device 18 is in the open position, allowing the high dielectric/high loss fluid (i.e., in this case, blood), to be closer to the antenna 16. In the closed position of device 18, the low dielectric/low loss plastic of device 18 will displace the blood producing an impedance mismatch and higher reflected power. The measured power difference shown by the power meter 56 provides a positive determination of, and indication to the physician of, the condition of the stand-off device, assuring that power will not be applied to antenna 16 if device 18 is closed and the catheter 10 is not spaced properly from the wall of blood vessel V.

One could also determine the condition of stand-off device by observing the amount of cord 22, e.g., number of beads 26, protruding from the end of fitting branch 15a in FIG. 1. Such an indicator is less desirable, however, because the cord could become separated from end segment 42b of sleeve 42 thereby invalidating the indication.

It will thus be seen that the objects set forth above, among those made apparent from the preceding description, are efficiently attained. Also, certain changes may be made in carrying out the above method and in the construction set forth without departing from the scope of the invention. For example, in some applications, RF frequencies may be used for heating in which case the RF antenna should be matched at the radiometric frequency. Also, sleeve 42 comprising stand-off device 18 may be formed so that its ribs 42a are normally bowed outward as shown in FIGS. 3 and 4. So long as catheter 10 is in introducer I (FIG. 1), the stand-off device remains closed. However, when the stand-off device leaves the confines of the introducer, it automatically opens and when the catheter is retracted into the introducer, the device 18 is squeezed back to its closed position. Further, it is also possible for sleeve end segment 42b to be fixed and segment 42a movable. Therefore, it is intended that all matter contained in the above description or shown in the accompanying drawings shall be interpreted as illustrative and not in a limiting sense.

Having described the invention, what is claimed as new and secured by letters patent are:

1. Intracorporeal warming apparatus comprising an elongated catheter for placement adjacent to high dielectric/high loss organic material in a patient, said catheter having a distal end and a proximal end and including an antenna adjacent said distal end and a cable having one end connected to said antenna and a second end;

a transmitter for transmitting a first signal of a first frequency capable of heating said material;

a receiver for receiving a second signal of a second frequency indicative of thermal radiation, said receiver producing an output signal in response thereto, and a diplexer connecting the second end of the cable to the transmitter and receiver, said diplexer coupling said first signal from said transmitter only to said antenna while coupling said second signal from said antenna only to said receiver so that the apparatus can simultaneously heat said material and determine the actual temperature of said material.

2. The apparatus defined in claim 1 wherein the receiver comprises a radiometer.

3. The apparatus defined in claim 1 wherein said catheter also includes expandable means located adjacent to said antenna, said expandable means being movable between a contracted position wherein the expandable means lies within the cross sectional envelope of the catheter and an expanded position wherein the expandable means extends outside said envelope, and moving means extending between said expandable means and the proximal end of the catheter for moving the expandable means between said positions.

4. The apparatus defined in claim 3 and further including means responsive to the position of the expandable means for indicating said position.

5. The apparatus defined in claim 1 wherein said antenna is a monopole.

6. The apparatus defined in claim 1 wherein said diplexer comprises a first arm connected between the transmitter and the antenna and containing a low pass filter which passes only said first signal, and a second arm connected between the receiver and a junction between the low pass filter and the antenna, said second arm containing a band pass filter which passes said second signal but blocks said first signal.

7. The apparatus defined in claim 6 wherein the length of the connection between the low pass filter and the junction is one-quarter of the wavelength of the second signal and the length of the connection between the band pass filter and the junction is one-quarter of the wavelength of the first signal.

8. The apparatus defined in claim 1 and further including a display responsive to said output signal for producing an indication of the actual temperature of said material.

9. The apparatus defined in claim 1 and further including control means responsive to said output signal for controlling the transmitter to heat said material according to a selected temperature/time profile.

10. An extracorporeal warming apparatus comprising an elongated, flexible catheter having a distal end and a proximal end, said catheter including coaxial inner and outer conductors separated by a dielectric medium, said inner conductor being longer than said outer conductor so that a segment of the inner conductor projects axially beyond the outer conductor adjacent the distal end of the catheter to form an antenna;

an expandable stand-off device adjacent to said antenna, said stand-off device including a flexible sleeve encircling said distal end segment of said inner conductor, said sleeve having one end fixed relative to said conductors and a second end movable parallel to said conductors between a first position wherein said sleeve is generally cylindrical and a second position wherein said sleeve is bowed outward, and moving means for moving the second end of the sleeve between said positions.

11. The apparatus defined in claim 10 wherein said sleeve is slitted lengthwise between said first and second ends to form a circular array of resilient ribs between said ends.

12. The apparatus defined in claim 10 wherein the moving means comprise a movable cord having one end attached to the second end of the sleeve and a second end projecting from the proximal end of the catheter so that by exerting a force on the second end of the cord, the second end of the sleeve may be moved to said second position.

13. The apparatus defined in claim 12 wherein said sleeve has a natural, unstressed state wherein said ribs are straight.

14. The apparatus defined in claim 11 wherein said sleeve has a natural, unstressed state wherein said ribs are bowed.

15. The apparatus defined in claim 10 wherein said one end of the sleeve is closer to the distal end of the catheter.

16. The apparatus defined in claim 10 wherein said one end of the sleeve is closer to the proximal end of the catheter.

17. The apparatus defined in claim 10 wherein the antenna is a monopole.

18. The apparatus defined in claim 10 wherein the antenna is a helical antenna.

19. The apparatus defined in claim 10 and further including an electrical cable having one end connected to said inner and outer conductors at the proximal end of the catheter and a second end adapted to be connected to a control and display unit.

20. The apparatus defined in claim 19 and further including a control and display unit comprising a transmitter for transmitting a first signal at a frequency capable of heating high-dielectric/high loss organic material adjacent to the catheter;

a receiver for receiving a second signal of a second frequency and indicative of thermal radiation, said receiver producing an output signal in response thereto, and a diplexer connecting the second end of said cable to the transmitter and receiver, said diplexer coupling said first signal from said transmitter only to said antenna while coupling said second signal from the antenna only to said receiver so that the apparatus can simultaneously heat said material and determine the actual temperature of said material.

21. The apparatus defined in claim 20 and further including a display responsive to said output signal for producing an indication of the actual temperature of said material.

22. The apparatus defined in claim 20 and further including control means responsive to said output signal for controlling the transmitter to heat said material according to a selected temperature/time profile.

* * * * *